United States Patent
Lipowsky et al.

(10) Patent No.: US 7,700,804 B2
(45) Date of Patent: Apr. 20, 2010

(54) PROCESS FOR TRANSFERRING HEAT TO A LIQUID MIXTURE COMPRISING AT LEAST ONE (METH)ACRYLIC MONOMER

(75) Inventors: Gunter Lipowsky, Schriesheim (DE); Volker Schliephake, Schifferstadt (DE); Steffen Rissel, Kirchheim (DE); Ulrich Jaeger, Roemerberg (DE); Frank Hoefer, Bad Duerkheim (DE); Sylke Haremza, Neckargemuend (DE); Peter Zurowski, Landau (DE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 191 days.

(21) Appl. No.: 11/962,461

(22) Filed: Dec. 21, 2007

(65) Prior Publication Data

US 2008/0149319 A1    Jun. 26, 2008

Related U.S. Application Data

(60) Provisional application No. 60/871,529, filed on Dec. 22, 2006.

(30) Foreign Application Priority Data

Dec. 22, 2006    (DE) .................. 10 2006 062 258

(51) Int. Cl.
*C07C 51/42* (2006.01)
(52) U.S. Cl. ..................................... 562/600
(58) Field of Classification Search ........ None
See application file for complete search history.

(56) References Cited

U.S. PATENT DOCUMENTS

| | | | |
|---|---|---|---|
| 3,271,296 A | 9/1966 | Gonzalez | |
| 4,317,926 A | 3/1982 | Sato et al. | |
| 5,897,749 A | 4/1999 | Kroker et al. | |
| 6,620,969 B1 * | 9/2003 | Nishimura et al. | 562/600 |
| 6,806,385 B1 | 10/2004 | Hammon et al. | |
| 7,279,075 B2 | 10/2007 | Thiel et al. | |
| 2005/0074563 A1 | 4/2005 | Tatsuzawa et al. | |
| 2005/0090628 A1 | 4/2005 | Eck et al. | |

FOREIGN PATENT DOCUMENTS

| | | |
|---|---|---|
| DE | 29 01 783 | 8/1979 |
| DE | 102 35 847 | 8/2003 |
| DE | 103 36 386 | 3/2004 |
| DE | 103 32 758 | 5/2004 |
| DE | 103 00 816 | 7/2004 |
| EP | 0 854 129 | 7/1998 |
| EP | 1 034 824 | 9/2000 |
| GB | 1 282 854 | 7/1972 |
| WO | WO 99/47482 | 9/1999 |

OTHER PUBLICATIONS

"Methacrylic Acid and Derivatives" in Kirk Othmer Encyclopedia of Chemical Technology, Copyright © 2003 by John Wiley & Sons, Inc., Article Online Posting Date: Mar. 14, 2003, pp. 227-270.*

* cited by examiner

*Primary Examiner*—Karl J Puttlitz
(74) *Attorney, Agent, or Firm*—Oblon, Spivak, McClelland, Maier & Neustadt, L.L.P.

(57) ABSTRACT

A process for transferring heat to a liquid mixture comprising at least one (meth)acrylic monomer in an indirect heat exchanger, wherein a quaternary ammonium salt, a tertiary amine or a salt thereof with a Brønsted acid is added to the liquid mixture to reduce fouling.

15 Claims, No Drawings

PROCESS FOR TRANSFERRING HEAT TO A LIQUID MIXTURE COMPRISING AT LEAST ONE (METH)ACRYLIC MONOMER

The present invention relates to a process for transferring heat to a liquid mixture comprising at least one (meth)acrylic monomer with the aid of an indirect heat exchanger which is flowed through on its primary side by a liquid heat carrier and on its secondary side simultaneously by the liquid mixture comprising at least one (meth)acrylic monomer.

In this document, the notation "(meth)acrylic monomers" is an abbreviation of "acrylic monomers and/or methacrylic monomers".

In this document, the term "acrylic monomers" is an abbreviation of "acrolein, acrylic acid, diacrylic acid and/or esters of acrylic acid".

In this document, the term "methacrylic monomers" is an abbreviation of "methacrolein, methacrylic acid and/or esters of methacrylic acid".

(Meth)acrylic monomers are important starting compounds for the preparation of polymers which find use, for example, as an adhesive or as water-superabsorbing materials.

In industry, (meth)acrolein and (meth)acrylic acid are prepared predominantly by catalytic gas phase oxidation of suitable $C_3/C_4$ precursor compounds (or of precursor compounds thereof), especially of propylene and propane in the case of acrolein and acrylic acid or isobutene and isobutane in the case of methacrylic acid and of methacrolein. In addition to propylene, propane, isobutene and isobutane, suitable starting materials are also other compounds comprising 3 or 4 carbon atoms, such as isobutanol, n-propanol or precursors thereof, for example the methyl ether of isobutanol.

(Meth)acrylic acid can also be obtained from (meth)acrolein (which is obtainable, for example, by condensation of propionaldehyde and formaldehyde).

This normally affords a product gas mixture from which the (meth)acrylic acid or the (meth)acrolein has to be removed.

Esters of (meth)acrylic acid are obtainable, for example, by direct reaction of (meth)acrylic acid and/or (meth)acrolein with the corresponding alcohols.

However, this case too also gives rise initially to product mixtures from which the (meth)acrylic esters have to be removed.

For the aforementioned removals, one or more thermal separating processes are frequently employed. In these processes, at least one stream comprising at least one (meth)acrylic monomer is generally supplied to a separating space, and at least one (different) stream comprising at least one (meth)acrylic monomer is withdrawn from the same separating space. A characteristic feature for the majority of thermal separating processes is that the separating action achieved with them generally requires the supply of thermal energy (the transfer of heat) and that they typically involve liquid phases (liquid mixtures) (which are conducted in the separating space) which comprise (meth)acrylic monomers (at least one (meth)acrylic monomer) (cf., for example, DE-A 10300816).

In general, this thermal energy (heat) is supplied with the aid of indirect heat exchangers. To this end, at least one liquid mixture comprising at least one (meth)acrylic monomer is frequently withdrawn from part of the separating space. This then flows through (for example with the aid of pumps and/or as a result of natural circulation) the secondary side of an indirect heat exchanger which is flowed through on its primary side simultaneously by a fluid heat carrier.

Owing to the temperature gradients existing between the two streams (the fluid heat carrier (in this document, this shall be understood to mean a liquid heat carrier, a gaseous heat carrier or a mixture of a liquid and a gaseous (vaporous) heat carrier) has a higher temperature than the liquid mixture comprising at least one (meth)acrylic monomer), heat exchange takes place through the solid material dividing wall which divides the primary side from the secondary side of the indirect heat exchanger (i.e., in this document, an indirect heat exchanger shall be a heat exchanger in which heat carrier and mixture to be heated are not in material contact with one another but rather are divided spatially from one another by a material dividing wall), from which heating of the liquid mixture comprising at least one (meth)acrylic monomer which flows through the secondary side results. Subsequently, the liquid mixture which comprises at least one (meth)acrylic monomer and leaves the secondary side of the indirect heat exchanger in heated form (in the course of heat exchange, this may also be converted partly or completely to the vapor phase; in this case, the heat exchanger is frequently also referred to as an evaporator; in this document, the terms "gaseous" and "vaporous" are used synonymously) is recycled at least partly into the same part of the separating space from which it has been withdrawn and/or into another part of this separating space, and the withdrawal point and the recycling point may be close to one another (cf., for example, DE-A 10332758).

However, a disadvantage of a procedure as described above is that (meth)acrylic monomers, in circumstances including the influence of elevated temperature and especially in the condensed phase, tend undesirably to the formation of high molecular weight compounds (polymers) of a wide variety of different types (free-radical polymers, polycondensates (e.g. Michael adducts) etc.). The addition of so-called polymerization inhibitors (useful polymerization inhibitors also include nitrogen-comprising compounds which bear at least one phenyl group on the nitrogen (e.g. N,N'-diisobutyl-para-phenylenediamine (Kerobit® BTD), N,N-diphenylamine, methylene blue, or phenothiazine; cf., for example, EP-A 1 062 197, DE-A 103 36 386 and DE-A 102 35 847, and also DE-A 29 01 783) which are capable of binding radicals which form randomly and initiate undesired free-radical polymerization to a certain degree) allows the aforementioned undesired formation of high molecular weight compounds to be prevented to a limited degree but unfortunately not completely (cf. DE-A 102 11 273), which is why, even when free-radical polymerization inhibitors are used, there is deposition of solids especially on the surface of the material dividing wall of the indirect heat exchanger which faces the secondary side in the course of an indirect heat transfer, to be performed as described, to the liquid mixture comprising at least one (meth)acrylic monomer in the course of time (also referred to in the literature in many cases as fouling), which reduces the heat transfer from the primary side to the secondary side (cf. U.S. Pat. No. 3,271,296). This solid deposition is also contributed to by factors including pyrolytic decomposition reactions (up to and including coke formation). From time to time, the thermal separating process therefore has to be interrupted in order to clean the material dividing wall of the indirect heat exchanger, in particular on its secondary side.

The prior art discloses different measures for reducing or delaying fouling on the secondary side of the indirect heat exchanger.

For the reduction of the formation of fouling, U.S. Pat. No. 3,271,296 recommends the addition of reaction products of propylenediamine with alkyl- and alkenyl-substituted succinic carboxylic acids to which dispersing action is attributed (for example Komad® 313 from Mol (Hungary)). In a corresponding manner, EP-A 1062197 recommends the addition of surfactants to the liquid mixture which comprises at least one (meth)acrylic monomer and is to be heated. For the reduction of the above-described fouling, EP-A 854129 in principle recommends the use of forced-circulation flash evaporators.

However, a disadvantage of the prior art recommendations is that the action of the additives recommended is not completely satisfactory. This is true in the same way for the mere use of forced-circulation flash evaporators.

It was therefore an object of the present invention to provide an improved process for transferring heat to a liquid mixture comprising at least one (meth)acrylic monomer with the aid of an indirect heat exchanger.

Accordingly, a process has been found for transferring heat to a liquid mixture comprising at least one (meth)acrylic monomer with the aid of an indirect heat exchanger which is flowed through (constantly) on its primary side by a liquid heat carrier and on its secondary side simultaneously by the liquid mixture comprising at least one (meth)acrylic monomer, wherein the liquid mixture comprising at least one (meth)acrylic monomer comprises at least one added active compound other than (meth)acrylic monomers from the group consisting of tertiary amines, the salts formed from a tertiary amine and a Brønsted acid, and quaternary ammonium compounds (the salts of quaternary ammonium ions), with the proviso that none of the tertiary and quaternary nitrogen atoms in the at least one active compound bears a phenyl group but at least some bear (at least one bears) at least one alkyl group.

As already stated, the term (meth)acrylic monomers shall comprise in particular the compounds acrolein, methacrolein, methacrylic acid and acrylic acid. However, diacrylic acid (olefinically unsaturated Michael adduct of two acrylic acid molecules) and the esters of acrylic acid or methacrylic acid and (preferably monohydric (having one hydroxyl group)) alcohols shall also be encompassed under this term. In other words, in particular, the esters of acrylic acid with (preferably monohydric (having one hydroxyl group)) $C_1$- to $C_8$-alkanols (in particular with the $C_4$- to $C_8$-alkanols) and the esters of methacrylic acid with (preferably monohydric (having one hydroxyl group)) $C_1$- to $C_8$-alkanols (in particular with the $C_4$- to $C_8$-alkanols) are also (meth)acrylic monomers in the context of this document. In other words, (meth)acrylic monomers are, for example, the following (meth)acrylic esters: hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate and 2-ethylhexyl methacrylate.

In this document, a tertiary amine shall be understood to mean an organic compound which comprises at least one nitrogen atom in chemically bound form, which has a chemical bond to three different carbon atoms (to no more than and no less than these three and also not to any other atom), with the proviso that none of the three carbon atoms simultaneously has a chemical double bond to an oxygen atom or another element of the group comprising oxygen in the Periodic Table of the Elements. In this document, such a nitrogen atom is referred to as a tertiary nitrogen atom.

In this document, a quaternary ammonium compound shall be understood to mean an ionic compound (the salt of a quaternary ammonium ion) which comprises at least one nitrogen atom which has a chemical bond (generally a covalent bond) to four different carbon atoms (and otherwise to no other atom), with the proviso that none of the four carbon atoms simultaneously has a chemical double bond to an oxygen atom or another element of the group comprising oxygen in the Periodic Table of the Elements. In this document, such a nitrogen atom is referred to as a quaternary nitrogen atom. The positively charged ion which comprises it is referred to in this document as a quaternary ammonium ion.

In this document, a phenyl group shall be understood to mean any aromatic ring consisting of six carbon atoms (the characteristic feature of such an aromatic ring system is that the six carbon atoms are within one plane in an X-ray diffraction experiment), irrespective of whether these six carbon atoms are chemically bonded to a hydrogen atom or to a substituent for the hydrogen atom. A tertiary or quaternary nitrogen atom bears a phenyl group when it is chemically (covalently) bonded to one of the six carbon atoms of the aromatic ring. In other words, triphenylamine, quinoline, phenothiazine and methylene blue are not active compounds in the context of this invention.

It will be appreciated that an active compound to be added in accordance with the invention may have more than one tertiary nitrogen atom or more than one quaternary nitrogen atom. Of course, an active compound to be added in accordance with the invention may also have at least one tertiary nitrogen atom and at least one quaternary nitrogen atom.

Relative to a particular tertiary amine, a Brønsted acid is such a chemical compound which is capable of releasing a proton to the tertiary amine, which converts the tertiary amine to a non-quaternary, electrically positively charged ammonium ion (cf. Grundlagen der organischen Chemie [Fundamentals of organic chemistry]; Hans Rudolf Christen; Verlag Sauerländer Aarau, Diesterweg●Salle Frankfurt am Main, 1975, p. 383 ff.). This simultaneously converts the Brønsted acid itself to its conjugated anionic base.

Active compounds particularly suitable in accordance with the invention are tertiary aliphatic amines and their non-quaternary ammonium salts. These amines can be derived from ammonia in that its three hydrogen atoms are replaced by three alkyl groups.

Among these tertiary aliphatic amines, preference is given to those of the general formula I (and the resulting non-quaternary ammonium salts):

(I)

where $R^1$, $R^2$ and $R^3$ are each independently an alkyl group which has from 1 to 8 carbon atoms, preferably from 1 to 6 carbon atoms and more preferably from 1 to 4 carbon atoms (these groups are formed only from hydrogen and carbon atoms and do not comprise the cycloalkyl groups) or cycloalkyl group (are likewise formed only from hydrogen and carbon).

Among the tertiary aliphatic amines of the general formula I, particular preference is given in turn to those in which $R^1=R^2=R^3$ (and preferably an alkyl group) (and the resulting non-quaternary ammonium salts (i.e. their salts with a Brønsted acid)).

Preferred $R^1$, $R^2$, $R^3$ radicals are the methyl group, the ethyl group, the isopropyl group, the n-propyl group, the n-butyl group, the tert-butyl group and the n-hexyl group, and also the cyclohexyl group.

In other words, active compounds particularly advantageous in accordance with the invention are, for example, trimethylamine, triethylamine, tri-n-hexylamine, tri-n-butylamine and N-ethyl-N,N-diisopropylamine (and their salts with a Brønsted acid).

Also useful as inventive active compounds are those (referred to later in this document as active compounds of the general formula II) which derive from the active compounds of the general formula (I) in a formal sense in that at least one of the $R^1$, $R^2$, $R^3$ radicals is an alkyl or cycloalkyl group in which one or more hydrogen atoms are replaced by at least one of the groups —OH, —$NH_2$, —$NHCH_3$ and —$N(CH_3)_2$ and/or the (cyclic or acyclic) carbon chain is interrupted at least once by an oxygen atom (and salts thereof with a Brønsted acid). Among these, particular emphasis should be given to N,N,N',N'-tetramethyl-1,3-propanediamine, N,N-diethylethanolamine, and also bis(2-dimethylaminoethyl)ether, pentamethyldiethylenetriamine, 3-dimethylamino-1-propylamine, N,N,N',N'-tetramethyl-1,6-hexanediamine and N,N-dimethylcyclohexylamine (and salts thereof with a Brønsted acid).

Useful further tertiary amines favorable in accordance with the invention (active compounds III) include derivatives of 1,3-diazole (imidazole) in which the hydrogen on the nitrogen of the 1,3-diazole in the 1-position has been replaced by an alkyl group $R^4$ having from 1 to 8 carbon atoms, preferably from 1 to 6 carbon atoms and more preferably from 1 to 4 carbon atoms, and/or the nitrogen of the 1,3-diazole in the 3-position has been alkylated with an alkyl group $R^5$ having from 1 to 8 carbon atoms, preferably from 1 to 6 carbon atoms and more preferably from 1 to 4 carbon atoms. In the case of the "and" linkage, the salts are the so-called imidazolium salts whose cation, in the context of the invention, has two tertiary nitrogen atoms. In the "or" case, the salts are imidazolium salts with only one tertiary nitrogen atom in the context of the invention.

Examples of such tertiary amines suitable in accordance with the invention are 1-methylimidazole, 1-ethylimidazole, 1-propylimidazole, 1-ethyl-3-methylimidazolium acrylate, 1-ethyl-3-methylimidazolium acetate, 1-n-butyl-3-methylimidazolium acetate and 1-ethyl-3-methylimidazolium chloride. Among the aforementioned imidazolium salts, preference is given in accordance with the invention to those whose anion is hydroxide ($^\ominus$OH) or the anionic conjugate base of a monobasic Brønsted acid (capable of releasing only one proton to a strong base such as sodium hydroxide; i.e. sulfuric acid is a dibasic Brønsted acid). These singly negatively charged anions include in particular the carboxylate anions of monobasic organic carboxylic acids, for example formic acid, acetic acid, propionic acid, acrylic acid, methacrylic acid, chloroacetic acid and nitroacetic acid. In particular, these singly negatively charged anions also include the conjugate bases of strong monobasic inorganic Brønsted acids such as HCl, HBr, HI, $HNO_3$ and $HClO_3$.

The aforementioned Brønsted acids (including water) are also those which are particularly suitable for converting tertiary amines suitable in accordance with the invention (especially the tertiary amines (I) and (II)) to salts thereof which are suitable in accordance with the invention (non-quaternary ammonium compounds).

A further group of active compounds suitable in accordance with the invention is that of quaternary ammonium compounds. These include in particular the salts of quaternary ammonium (cat)ions and the anionic conjugate bases of Brønsted acids (for example the salts of DE-A 10314203), especially of monobasic Brønsted acids. These preferred singly negatively charged anions include in particular $^\ominus$H, the carboxylate ions of monobasic organic carboxylic acids, for example formic acid, acetic acid, propionic acid, acrylic acid, methacrylic acid, chloroacetic acid and nitroacetic acid. In particular, these singly negatively charged anions also include the conjugate bases of monobasic inorganic Brønsted acids. Such anions are, for example, $Cl^\ominus$, $Br^\ominus$, $I^\ominus$, $NO_3^\ominus$ and $ClO_3^\ominus$.

Preferred quaternary ammonium (cat)ions are in particular those which are obtainable from the active compounds (I) and (II) in a formal sense by binding, to their tertiary nitrogen atom, a further alkyl group $R^6$ having from 1 to 8 carbon atoms, preferably from 1 to 6 carbon atoms and more preferably from 1 to 4 carbon atoms.

Such quaternary ammonium ions are encompassed under the general formula (IV)

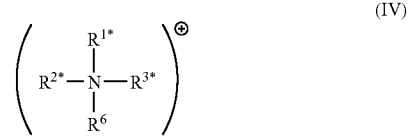

(IV)

where $R^{1*}$, $R^{2*}$ and $R^{3*}$ are each independently, and independently of $R^6$, an alkyl group or cycloalkyl group which has from 1 to 8 carbon atoms, preferably from 1 to 6 carbon atoms and more preferably from 1 to 4 carbon atoms, or one of the abovementioned alkyl or cycloalkyl groups in which one or more hydrogen atoms are replaced by at least one of the groups —OH, —$NH_2$, —$NHCH_3$ and —$N(CH_3)_2$ and/or the (cyclic or acyclic) carbon chain is interrupted at least once by an oxygen atom.

Particularly preferred quaternary ammonium ions IV are those of the general formula (V)

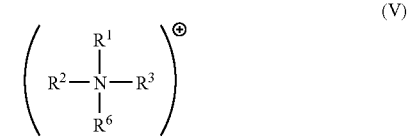

(V)

in which $R^1$, $R^2$, $R^3$ and $R^6$ may each independently have the definition assigned to these radicals in this document.

Particularly preferred quaternary ammonium ions (V) are those where $R^1=R^2=R^3=R^6$ (and preferably an alkyl group).

Examples of quaternary ammonium compounds very particularly preferred in accordance with the invention are tetramethylammonium acetate, tetramethyl-ammonium chloride, tetramethylammonium hydroxide and tetramethylammonium acrylate.

In principle, all $R^1$, $R^2$, $R^3$, $R^4$, $R^5$, $R^6$ and $R^{1*}$, $R^{2*}$ and $R^{3*}$ radicals, in the case that they are not cyclic, may be either straight-chain or branched.

In general, for the process according to the invention, at least 0.01% by weight, or at least 0.05% by weight, often from 0.1 to 10% by weight, frequently from 0.1 to 5% by weight, in many cases from 0.1 to 3% by weight and preferably from 0.5 to 2% by weight or from 0.5 to 1% by weight (based in each case on its weight) of at least one inventive active compound will be added to the liquid mixture comprising at least one (meth)acrylic monomer.

Advantageously in accordance with the invention, the active compounds to be added in accordance with the invention are such that they dissolve completely in the particular amount added in the liquid mixture comprising at least one (meth)acrylic monomer under the use conditions of the process according to the invention (working pressure, working temperature).

Against this background, preference is given to those active compounds to be added in accordance with the invention whose molar mass is $\leq$600 g, better $\leq$500 g, advantageously $\leq$400 g, favorably $\leq$300 g, preferably $\leq$250 g, more preferably $\leq$200 g and most preferably $\leq$180 g. Normally, the molar mass of active compounds to be added in accordance with the invention will, however, be $\geq$59.1 g.

The liquid mixtures to be heated in accordance with the invention may comprise the at least one (meth)acrylic monomer either in more or less pure form or in diluted form (for example with solvents). The solvent may be either an aqueous solvent or an organic solvent. This means that a liquid mixture to be heated in accordance with the invention may (based on its weight) comprise, for example, $\geq$0.05% by weight, or $\geq$0.1% by weight, or $\geq$0.5% by weight, or $\geq$1% by weight, or $\geq$1.5% by weight, or $\geq$2% by weight, or $\geq$10% by weight, or $\geq$20% by weight, or $\geq$40% by weight, or $\geq$60% by weight, or $\geq$80% by weight, or $\geq$90% by weight, or $\geq$95% by weight, or $\geq$99% by weight of the at least one (meth) acrylic monomer. Of course, the content of a particular (meth) acrylic monomer is always at values of <100% by weight (the above is simultaneously the definition of the term "liquid mixture comprising at least one (meth)acrylic monomer", as used in this document; it means a liquid substance which, in addition to at least one particular (meth)acrylic monomer, also comprises at least one second (meth)acrylic monomer and/or at least one second substance other than a (meth) acrylic monomer; the proportions may be completely as desired, provided only that they can be detected analytically (for example by gas chromatography or by means of HPLC); for example, the second substance other than a (meth)acrylic monomer may be a polymerization inhibitor).

At this point, it should be emphasized that all statements made in this document are valid especially when the at least one (meth)acrylic monomer is acrylic acid. The disclosure content of this document shall therefore in particular also comprise those statements which result from the replacement of the term "(meth)acrylic monomer(s)", wherever it occurs in this document, with "acrylic acid".

The temperature with which the liquid mixture comprising at least one (meth)acrylic monomer leaves the indirect heat exchanger again (i.e. on completion of the inventive transfer of heat) ($T^{out}$) will generally be from 50 to 350° C., or from 100 to 300° C., frequently from 150 to 250° C., and often from 170 to 220° C. The pressure within the indirect heat exchanger may be either atmospheric pressure (1 atm) or above or below atmospheric pressure. Typical pressure ranges suitable for the inventive heat transfer are from 1 mbar to 10 bar, often from 10 mbar to 5 bar and in many cases from 50 mbar to 3 bar. The temperature with which the liquid mixture comprising at least one (meth)acrylic monomer enters the indirect heat exchanger in the process according to the invention, in order to be heated therein ($T^{in}$) may, for example, be from 50 to 350° C., frequently from 70 to 250° C. and in many cases from 120 to 220° C. The difference between $T^{in}$ and $T^{out}$, i.e. the difference $T^{out}-T^{in}$, will generally be from 0.1 to 50° C., frequently from 0.5 to 25° C. and in many cases from 1 to 10° C. The working pressure of the liquid mixture comprising at least one (meth)acrylic monomer, on entry thereof into the indirect heat exchanger, is greater than on exit from the at least one heat exchanger. In principle, the liquid mixture comprising at least one (meth) acrylic monomer, when it exits from the indirect heat exchanger, may be converted completely to the vapor phase (gas phase).

Otherwise, the liquid mixture comprising at least one (meth)acrylic monomer generally also comprises added polymerization inhibitors against free-radical polymerization. Useful such inhibitors are in principle all of those which are recommended in the prior art for the purpose of inhibiting free-radical polymerization of (meth)acrylic monomers present in the liquid phase. Useful such polymerization inhibitors include alkylphenols, for example o-, m- or p-cresol (methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol, 2-methyl-4-tert-butylphenol, 4-tert-butyl-2,6-dimethylphenol, or 2,2'-methylenebis(6-tert-butyl-4-methylphenol), hydroxyphenols, for example hydroquinone, 2-methylhydroquinone, 2,5-di-tert-butylhydroquinone, pyrocatechol (1,2-dihydroxybenzene) or benzoquinone, aminophenols, for example para-aminophenol, nitrosophenols for example para-nitrosophenol, alkoxyphenols, for example 2-methoxyphenol (guaiacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol, tocopherols, for example o-tocopherol, and 2,3-dihydro-2,2-dimethyl-7-hydroxybenzofuran (2,2-dimethyl-7-hydroxycoumaran), N-oxyls such as 4-hydroxy-2,2,6,6-tetramethylpiperidine N-oxyl, 4-oxo-2,2,6,6-tetramethylpiperidine N-oxyl, 4-acetoxy-2,2,6,6-tetramethylpiperidine N-oxyl, 2,2,6,6-tetramethylpiperidine N-oxyl, 4,4',4''-tris(2,2,6,6-tetramethylpiperidine N-oxyl) phosphite or 3-oxo-2,2,5,5-tetramethylpyrrolidine N-oxyl, aromatic amines or phenylenediamines, for example N,N-diphenylamine, N-nitrosodiphenylamine and N,N'-dialkyl-para-phenylenediamine, where the alkyl radicals may be the same or different and each independently consist of from 1 to 4 carbon atoms and may be straight-chain or branched, hydroxylamines, for example N,N-diethylhydroxylamine, phosphorus compounds, for example triphenylphosphine, triphenyl phosphite, hypophosphorous acid or triethyl phosphite, sulfur compounds, for example diphenyl sulfide or phenothiazine, if appropriate in combination with metal salts, for example the chlorides, dithiocarbamates, sulfates, salicylates or acetates of copper, manganese, cerium, nickel or chromium. It will be appreciated that it is also possible to use a wide variety of different mixtures of the polymerization inhibitors mentioned. The polymerization inhibitor used is preferably phenothiazine and/or hydroquinone monomethyl ether. In many cases, the named polymerization inhibitors are supported by a molecular oxygen-comprising gas (for example air or nitrogen-diluted air). Depending on the polymerization inhibitor used, its use amount in the liquid mixture comprising at least one (meth)acrylic monomer will be from 10 to 1000 ppm by weight, frequently from 50 to 500 ppm by weight and in many cases from 150 to 350 ppm by weight (based in each case on the total content of (meth)acrylic monomers in the liquid mixture).

In the indirect heat exchanger, the heat transfer does not occur in the direct contact, forced by mixing, between fluid heat carrier and liquid mixture to be heated. Instead, the heat transfer proceeds indirectly between the fluids divided by a dividing wall. The dividing surface of the heat transferer (heat exchanger) which is active for the heat transport is referred to as a heat exchange or transfer surface, and the heat transport follows the known laws of heat transfer.

It is essential in accordance with the invention that, in the process according to the invention, the indirect heat exchanger is flowed through both by the liquid heat carrier and by the liquid mixture comprising at least one (meth) acrylic monomer. In other words, both flow into the heat exchanger and then back out again.

Useful fluid heat transferers for the process according to the invention are in principle all possible hot gases, vapors and liquids. This primarily includes steam which can be at different pressures and temperatures. Frequently, it is favorable when the steam condenses as it flows through the indirect heat exchanger (saturated steam). Alternative useful heat carriers are oils, melts, organic liquids and hot gases. Examples thereof are silicone compounds such as tetraaryl silicate, diphenyl mixture composed of 74% by weight of diphenyl ether and 26% by weight of diphenyl, chlorinated noncombustible diphenyl, and mineral oils and pressurized water.

Indirect heat exchangers suitable in accordance with the invention are in particular double tube, tube bundle, ribbed tube, spiral or plate heat transferees. Double tube heat transferers consist of two tubes, one of which is inside the other. A plurality of these double tubes can be combined to give tube walls. The inner tube may be smooth or be provided with ribs to improve the heat transfer. In individual cases, it is also possible for a tube bundle to replace the inner tube. The fluids which exchange heat move in cocurrent or in countercurrent. The liquid mixture comprising at least one (meth)acrylic monomer flows, in accordance with the invention, appropriately upward in the inner tube, and, for example, hot steam downward in the ring space. Tube diameters adjusted to the desired throughput impart flow rates which give rise to high heat transfer numbers to the fluid media.

The temperature difference between fluid heat carrier and the fluid mixture comprising at least one (meth)acrylic monomer may, within the indirect heat exchanger, quite generally, for example, be from 5° C. to 150° C., frequently from 10° C. to 100° C., or from 20° C. to 80° C.

Tube bundle heat transferers consist normally of a sealed wide outer tube which encloses the numerous smooth or ribbed transferer tubes of small diameter secured to tube plates. The distance from tube center to tube center of the bundled tubes is, appropriately from an application point of view, from 1.3 to 2.5 times the tube outer diameter. The large specific heat exchange area which arises—as an exchange area per unit of space requirement—is an advantage of the tube bundle heat transferee. The tube bundle heat transferers arranged vertically or horizontally differ in aspects including the tube shape. The transferer tubes may be straight, bent in a U shape or else be designed as a multipiece spiral tube bundle. The liquid mixture which comprises at least one (meth) acrylic monomer and is to be heated in accordance with the invention flows, preferably in accordance with the invention, within the transferer tubes (in principle, it may, though, also flow within the space surrounding the transferer tubes and the heat carrier in the transferer tubes). The fluid heat carrier (preferably saturated steam) flows, appropriately in accordance with the invention, outside the transferer tubes. Guide plates for better conduction of the fluid heat carrier in the outer chamber are appropriate in accordance with the invention and generally serve the additional purpose of supporting the transferer tubes. The guide plates generally increase the flow rates in the outer chamber and, inter alia, hence the heat transfer numbers. The flow in the outer chamber advantageously runs transverse to the transferer tubes. According to the flow direction of the outer chamber fluid in relation to the transferer tubes, it is possible to distinguish, for example, between longitudinal flow and cross flow and transverse flow tube bundle heat transferees. In principle, the fluid heat carrier can also be moved around the transferer tubes in a meandering manner, and conducted in cocurrent or countercurrent to the liquid mixture to be heated in accordance with the invention only viewed over the tube bundle heat exchanger. Spiral tube bundle heat transferers generally also utilize the advantages of cross flow. The tubes alternate—from layer to layer—from right to left. The outer chamber fluid flows in countercurrent to the tube fluid and flows around the spiral tubes in cross flow.

In the single-flow tube bundle heat transferee, the liquid mixture which comprises at least one (meth)acrylic monomer and is to be heated in accordance with the invention moves through all transferer tubes in the same direction.

Multiflow tube bundle heat transferers comprise tube bundles divided into individual sections (in general, the individual sections comprise an identical number of tubes). Dividing walls divide chambers which adjoin the tube plates (through which the transferer tubes are conducted with sealing and to which they are secured) into sections and deflect the liquid mixture which comprises at least one (meth)acrylic monomer and enters the chamber part from one section into a second section and hence back. The liquid mixture to be heated in accordance with the invention flows, according to the number of sections, through the length of the tube bundle heat transferer more than once (twice, three times, four times, etc.) with high speed in alternating direction (two-flow, three-flow, four-flow, etc. tube bundle heat transferer). Heat transfer number and exchange path increase correspondingly.

Plate heat transferers (plate heat exchangers) are normally composed in the manner of filter presses, generally of corrugated or otherwise profiled plates provided with channels for the liquid heat carrier and the liquid mixture to be heated (generally composed of graphite or metal, for example stainless steel) in a compact design. The two heat-exchanging fluids then flow in cocurrent, countercurrent and/or crosscurrent as thin layers alternating (for example upward and downward) through their chamber series and are in heat transfer with one another at both chamber walls. The corrugated plate profiles increase the turbulence and improve the heat transfer numbers. Plate heat exchangers suitable for the inventive purpose are, for example, described in EP-A 107 9194, U.S. Pat. No. 6,382,313, EP-A 123 2004 and WO 01/32301. Tube bundle heat exchangers are, for example, described in EP-A 700 893, EP-A 700 714 and DE-A 443 1949. Spiral tube and ribbed tube heat exchangers are described, for example, in Vauck/Müller, Grundoperationen chemischer Verfahrenstechnik [Basic operations in chemical process technology], 4th edition, Verlag Theodor Steinkopf, Dresden (1974) and in Ullmanns Encyclopädie der technischen Chemie, volume 2, Verfahrenstechnik I (Grundoperationen) [Process technology I (basic operations)], 4th edition, 1972, p. 432 ff.

Heat exchangers very particularly suitable for the process according to the invention are the heat exchangers described in EP-A 854 129 as prior art and as the invention (especially those depicted in FIGS. 1 to 3). These include in particular the forced-circulation tube evaporator, the forced-circulation tube flash evaporator and the Robert evaporator. In this context, the term "forced circulation" means that the liquid mixture comprising at least one (meth)acrylic monomer is conveyed with the aid of a pump through the indirect heat exchanger (its tubes), while the conveying in the tube bundle Robert evaporator is effected by virtue of the ascending boiling vapor bubbles and the density difference. EP-A 854 129 therefore forms a constituent integrated into this document.

The process according to the invention is suitable in particular for those liquid mixtures which comprise at least one (meth)acrylic monomer and, in a thermal separating process for separating a mixture comprising at least one (meth)acrylic monomer, are withdrawn from part of a separating space, to which is fed at least one stream comprising at least one (meth)acrylic monomer and from which is withdrawn at least one stream which differs therefrom and comprises at least one (meth)acrylic monomer, is conducted (conveyed) with the aid of pumps and/or by means of natural circulation through the secondary side of the indirect heat exchanger and, after leaving the indirect heat exchanger in liquid and/or vaporous form, is recycled or fed at least partly into the same part of the separating space from which it has been withdrawn, and/or into another part of the same separating space and/or into part of another separating space.

Frequently, the separating space comprises a separating column which comprises separating internals (but may in principle also comprise a separating column free of separating internals) (cf., for example, DE-A 10300816). The separating internals used in the separating space, for example in the separating column, fulfill the purpose of increasing the surface area for heat and mass transfer in the separating space, which brings about the separation in a thermal separating process. Useful such internals include, for example, random packings, structured packings and/or mass transfer trays of any type (cf., for example, all internals mentioned individually in DE-A 10336386).

Examples of such thermal separating processes are rectification, desorption, stripping, distillation, azeotropic rectification and the superimposition of adsorption and rectification. All of these processes are those in which gaseous (ascending) and liquid (descending) streams are conducted in countercurrent into the separating columns comprising separating internals, heat and mass transfer taking place owing to the gradients which exist between the streams and ultimately causing the separation desired in the separating column. In the thermal separating process of stripping (a stripping gas takes up components dissolved in a liquid with different affinity) and desorption (the reverse process of absorption; the matter dissolved in the liquid phase is removed by lowering the partial pressure; desorption and stripping are frequently employed superimposed on one another), the separating action is based in particular on the different solubility of (meth)acrylic monomers and other secondary components in a liquid. In distillation and rectification, the resulting separating action is based in particular on the difference in the boiling points of (meth)acrylic monomers and secondary components. Azeotropic distillation and rectification utilize the different degree to which (meth)acrylic monomers and secondary components tend to form azeotropes with added azeotroping agents.

The process according to the invention is of significance especially when, in a thermal separating process, a liquid stream comprising at least one (meth)acrylic monomer (to be treated under separating action) (e.g. acrylic acid or methacrylic acid) is conducted for separating purposes into a separating column comprising separating internals, and the liquid mixture which comprises at least one (meth)acrylic monomer and is to be heated in accordance with the invention is withdrawn from the separating space comprising the separating column below the feed point of the (liquid) stream to be treated under separating action into the separating column, is heated in accordance with the invention with the aid of an indirect heat exchanger and is recycled thus heated below the feed point of the (liquid) stream to be treated under separating action into the separating column, into the separating space comprising the separating column.

The above is true especially when acrylic acid or methacrylic acid is the (meth)acrylic monomer and the liquid stream to be treated with separating action is essentially that liquid phase which is formed when the acrylic acid or methacrylic acid is converted from the product gas mixture of a heterogeneously catalyzed partial gas phase oxidation for preparing acrylic acid or methacrylic acid from a $C_3$ or $C_4$ precursor compound by absorptive and/or condensative measures out of the product gas mixture into the liquid phase (cf., for example, DE-A 103 363 86, WO 01/96271, DE-A 196 316 45, DE-A 195 013 25, EP-A 982 289, DE-A 198 388 45, WO 02/076917, EP-A 1695 954, EP-A 695 736, EP-A 778 225, EP-A 1041 062, EP-A 982 287, EP-A 982 288, US 2004/024 2826, EP-A 792 867, EP-A 784 046, EP-A 695 736, EP-A 112 5912 and the literature cited on this subject in these documents, and also German application 102006049939.5).

This is true especially when the separating column is operated under reduced pressure (for example a top pressure of from 20 to 100 mbar, or to 150 mbar) and the recycling temperature out of the indirect heat exchanger into the separating space is $\geq 150°$ C., or $\geq 180°$ C., or $\geq 200°$ C., or $220°$ C. or more.

In principle, the nitrogen-comprising active compound to be added in accordance with the invention can be metered into the indirect heat exchanger only briefly before the entry of the liquid mixture to be heated in accordance with the invention and/or actually into the separating space from which the liquid mixture to be heated in accordance with the invention is withdrawn. Since high-boiling fraction is also normally discharged from the separating space, further active compound generally has to be metered in constantly.

Frequently, the separating columns with separating internals used for thermal separating processes are those which comprise a sequence of mass transfer trays at least as some of the separating internals. Mass transfer trays fulfill the purpose of providing locations with continuous liquid phases in the form of liquid layers in the separating column. The surface of the vapor or gas stream which, for example, ascends in the liquid layer and is thus distributed in the continuous liquid phase is then the crucial mass transfer surface. Mass transfer trays preferably conclude sealed to the wall surrounding them.

A classic among the mass transfer trays is the sieve tray. In this document, this refers to plates whose passages for the ascending gas or vapor phase are simple holes and/or slots.

The sieve trays are typically differentiated into two groups, i.e. into those with forced liquid flow and those without forced liquid flow.

Quite generally, forced liquid flow in mass transfer trays is achieved by the mass transfer trays having at least one downcomer (drain), through which the liquid, irrespective of the flow path of the vapor, flows from the upper tray to the lower tray (feed). The horizontal liquid flow over the transfer trays from feed to drain is selected in accordance with the process objective. The gas or the vapor passes through the open cross sections of the tray plate.

When the liquid is conducted over the tray in reverse flow (feed and drain of the mass transfer tray are disposed on the same side of the tray), these are referred to as reverse flow trays. In radial flow trays, the liquid flows radially on the tray from the middle (feed) to the drain at the edge of the tray.

In the crossflow trays, viewed over the entire flow area, the liquid is conducted transversely over the tray from feed to drain. In general, crossflow trays have a single-flow configuration. In other words, feed and drain are disposed on opposite sides of the tray. However, they may also have a double-flow (or else more than double-flow) configuration. In this case, the feed may be disposed, for example, in the middle and one drain on each of the opposite sides of the mass transfer tray.

In other words, the forced liquid flow in sieve trays is achieved by virtue of the sieve trays having, in addition to the passages for the ascending gas or vapor phase, at least one downcomer (drain), through which the liquid, irrespective of the flow path of the vapor, flows from the upper tray to the next lowest tray (feed). The liquid flows, for example, in transverse flow over the tray from at least one feed to at least one drain, in which case the feed pipe and drainpipe guarantee the liquid seal and the desired liquid height on the tray. Frequently (especially in the case of low column diameters), the sieve trays with forced liquid flow have a single-flow configuration. In other words, feed and drain are disposed on opposite sides of the tray. However, they may also have a double-flow (or else more than double-flow) configuration. In this case, the feed may be disposed, for example, in the middle and one drain on each of the opposite sides of the mass transfer tray. Such sieve trays are to be referred to hereinbelow as forced sieve trays. In these trays, trickle-through of the liquid which reduces the separating action is not, as in the case of hydraulically sealed crossflow trays, prevented by chimneys, into which the passages continue, but rather a minimum vapor loading is required for this purpose. The vapor ascends through the passages and bubbles through the liquid layer maintained by the drainpipe.

The dual-flow trays, or else trickle sieve trays, differ from the forced sieve trays in that they comprise no drain segment. The absence of drain segments (downcomers) in the dual-flow trays results in the ascending gas and the liquid descending in the separating column passing through the same passages of the tray. As in the case of forced sieve trays, a minimum vapor loading is also required in the case of dual-flow trays, in order to achieve appropriate separating action. When the vapor loading is significantly lower, ascending gas and descending reflux move past each other substantially without exchange and the tray is at risk of running dry.

In other words, in the case of dual-flow trays too, a lower limiting rate has to be present so that a certain liquid layer is maintained on the tray, in order to allow the tray to work. In the normal working range, the liquid in dual-flow trays trickles through the passages from tray to tray, and the continuous gas phase between the trays is interspersed by a divided liquid phase.

Compared to sieve trays, it is a characteristic feature of hydraulically sealed crossflow trays that they cannot run dry when the column is shut down, disregarding the tiny emptying drillhole (its cross section is normally more than 200 times smaller than the total cross section of the passages) which each crossflow tray has for reasons of utility.

In other words, even at low column loadings, hydraulically sealed crossflow trays have accumulated liquid (reflux and/or feed liquid) and are at no risk of running dry. This results from the fact that the passages of hydraulically sealed crossflow trays are not chimneyless drillholes, as is the case in sieve trays. Instead, each passage opens into a chimney which prevents the tray from running dry. Above the chimney, vapor deflecting hoods (bubble-caps) are mounted which are immersed in the accumulated tray liquid. Frequently, the vapor deflecting hoods are slotted or serrated at their edges (i.e. they have transport slots). The vapor stream ascending through the passage is deflected by the vapor deflecting hoods and flows parallel to the tray, i.e. at right angles to the column, into the accumulated liquid.

The vapor bubbles leaving adjacent hoods which are generally distributed equidistantly over the tray form a froth layer in the accumulated liquid.

Drainpipes or drain segments which leave trays, generally to the left or right in alternation, supported by weirs, control the liquid level of the mass transfer trays and feed the liquid to the tray below. It is essential for the hydraulically sealing action that the drainpipes or drain segments of the upper tray are immersed in the accumulated liquid of the tray below. There are preferably no feed weirs. Height-adjustable bubble-caps allow adaptation to the flow conditions and the equalization of the immersion depths in the event of production irregularities, so that all bubble-caps of the tray have uniform gas flow.

Depending on the design and arrangement of the bubble-caps, the hydraulically sealed crossflow trays having single-flow configuration are divided, for example, into round bubble-cap trays (passage, chimney and bubble-cap are round), tunnel-cap trays (passage, chimney and bubble-cap are rectangular, the bubble-caps are arranged in succession with the longer rectangular edge aligned parallel to the crossflow direction of the liquid) and Thormann trays (passage, chimney and bubble-cap are rectangular, the bubble-caps are arranged in succession with the longer rectangular edge at right angles to the crossflow direction of the liquid).

In this document, valve trays are crossflow trays which have tray drillholes having limited-stroke plate, ballast or lifting valves (floating flaps) which adapt the size of the vapor passage to the particular column loading. The ascending gas stream is deflected, flows parallel to the tray into the accumulated reflux liquid and forms a froth layer. Drainpipes equipped with weirs conduct the reflux from tray to tray. Frequently, they have double-flow configuration. However, they may also have triple-flow and multiflow (for example up to octuple-flow) configuration.

Mass transfer trays on which there is equilibrium between descending liquid and ascending vapor are referred to as theoretical plates.

This term can be applied to all other separating internals which are suitable for countercurrent distillations (rectifications) (such as structured packings and random packings) and to other thermal separating procedures such as desorption and stripping.

It is therefore appropriate to refer generally to theoretical plates. A theoretical plate is defined as the spatial unit which brings about enrichment in accordance with the thermodynamic equilibrium.

Frequently, acrylic acid from the product gas mixture of a heterogeneously catalyzed gas phase partial oxidation of at least one $C_3$ precursor compound of acrylic acid (e.g. propylene, acrolein and/or propane) at elevated temperature with molecular oxygen is converted to the liquid phase over catalysts in the said state, for example, by passing the hot product gas mixture comprising acrylic acid, if appropriate after indirect and/or direct cooling thereof, into a condensation column provided with separating internals (preferably mass transfer trays) and allowing it to ascend into itself within the condensation column, which fractionally condenses it, and withdrawing crude acrylic acid from the condensation column in a side draw, whose acrylic acid content is generally $\geq 90\%$ by weight, in many cases even $\geq 95\%$ by weight (cf., for example, DE-A 102 358 47, WO 2000/53560, DE-A 102 436 25, WO 2004/035514 and DE-A 103 327 58). The thermal energy required for this separation of the product gas mixture of the gas phase partial oxidation is essentially actually delivered with the hot product gas mixture.

As the outlet for secondary components having a higher boiling point than acrylic acid, bottoms liquid comprising these secondary components is withdrawn from the bottom of the condensation column, or high boiler fraction or a mixture of such bottoms liquid and high boiler fraction comprising these secondary components is withdrawn via a side draw below the side draw for the crude acrylic acid (all referred to hereinafter generically as high boiler liquid). A portion of the aforementioned high boiler liquid can be used for direct cooling of the product gas mixture of the gas phase partial oxidation and can be recycled into it in the high boiler region of the condensation column via this direct cooling. The high boiler liquid which has been withdrawn from the condensation column and has not been recycled into the condensation column in this way still comprises comparatively large amounts of acrylic acid. In order to prevent this acrylic acid being sent to disposal together with the high-boiling secondary components (i.e. in order to increase the yield of acrylic acid), the high boiler liquid is therefore advantageously subjected to a stripping at elevated temperature before this disposal. The stripping gas used is appropriately residual gas which leaves the condensation column at its top and comprises in particular the least condensable constituents of the product gas mixture of the gas phase partial oxidation. To this end, an appropriate portion thereof is appropriately compressed and superheated (generally to the temperature existing in the bottom of the stripping column). The stripping itself is, advantageously in accordance with the application, performed in a rectification column (stripping column) which comprises separating internals (preferably equidistant trickle sieve trays), in whose lower part (lower third of the theoretical plates) the high boiler liquid to be stripped is advantageously fed in.

In order to ensure maximum stripping efficiency, in a controlled manner, an acrylic acid-comprising liquid mixture is withdrawn continuously from the bottom of the stripping column, conducted through an indirect heat exchanger I for the purpose of heating it (generally a forced-circulation heat exchanger (frequently a forced-circulation tube bundle heat transferer), frequently a forced-circulation flash heat exchanger (in many cases a forced-circulation tube bundle flash heat transferer)) and then predominantly conveyed back into the rectification column in heated form (appropriately into the bottom). The stripping gas is preferably likewise fed to the bottom of the stripping column. The other portion of the bottoms liquid from the stripping column which has been heated in the heat exchanger I is conducted with viscosity (preferred), density or temperature control into a vessel, degassed therein and fed to residue incineration diluted with methanol.

In the stripping column, an acrylic acid-comprising mixture ascends. Reflux liquid is advantageously conducted in countercurrent above the feed point of the high boiler liquid in order to ensure increased separating action especially with respect to the high-boiling secondary components whose boiling point is not very different from that of acrylic acid. To obtain the reflux liquid, the gas mixture which has been conducted, for example, through a chimney tray which concludes the separating internals in the upper region of the stripping column is cooled beyond it by direct cooling in a spray cooler and partially condensed. The condensate consisting predominantly of acrylic acid is collected from the chimney tray, which simultaneously functions as a collecting tray, and withdrawn therefrom. A portion is cooled in an indirect heat exchanger II (preferably a plate heat exchanger) (for example by means of water as a heat carrier) and then used again (recycled) as cooling liquid for direct spray cooling. For the purpose of inhibiting polymerization, a further amount of high boiler liquid (which comprises polymerization inhibitors and stems from the condensation column) which is to be stripped is advantageously supplied to the portion or entire amount of the condensate withdrawn for this purpose before it is cooled in the indirect heat exchanger II, and a portion of the resulting mixture, before it enters the heat exchanger II, is recycled into the stripping column as reflux liquid essentially immediately below the chimney tray. If required, a portion of condensate withdrawn from the chimney tray may also be recycled directly into the bottom of the condensation column.

The gas stream which has not been condensed in the spray cooling, escapes from the stripping column in gaseous form and carries the acrylic acid which has been stripped free is, appropriately in accordance with the application, combined with the product gas mixture coming from the gas phase partial oxidation (preferably, for example, in the course of the direct cooling thereof or recycled into the bottom region of the condensation column (preferably not immersed)). The amount of residual gas which leaves the condensation column and is not used for stripping is, if required, recycled partly as inert diluent gas into the heterogeneously catalyzed gas phase partial oxidation and the remaining amount not usable there is disposed of, for example incinerated.

The working pressure within the stripping column is regularly above atmospheric pressure. Above the separating internals in the stripping column, working pressures of from 1.3 to 2 bar are typical. The reflux liquid for the stripping column can in principle also be generated outside the stripping column. The liquid in the bottom of the stripping column is preferably in the boiling state. When the heat exchanger I is designed as a forced-circulation tube bundle flash heat transferee, in contrast to the case of a pure forced-circulation tube bundle heat transferee, it is normally separated from the stripping column by a throttle device (for example in the simplest case by a perforated plate; alternatively, a valve is also possible). A portion of the acrylic acid-comprising, preferably boiling bottoms liquid at a phase interface pressure $P_x$ is withdrawn continuously from the stripping column and pumped by means of a circulation pump into the inflows of a tube bundle heat exchanger. A fluid heat carrier (for example hot steam; i.e. steam under pressure), whose temperature is above the temperature of the bottoms liquid in the stripping column, flows around the internal tubes of the tube bundle heat transferee. On the path through the inflow and outflow tubes of the tube bundle heat exchanger, the bottoms liquid withdrawn from the stripping column is heated by indirect heat exchange to a temperature $T_{y'}$ which is above the temperature of the bottom of the stripping column. The throttle device already mentioned separates the tube bundle heat transferer and the stripping column on the pressure side and enables, by virtue of suitable selection of the circulation pump output, the establishment of a throttle pressure $P_y$ which is above $P_x$ and is above the boiling pressure $P_{y'}$, corresponding to the temperature $T_{y'}$, of the stripping column bottoms liquid withdrawn. The aforementioned measures suppress boiling of the stripping column bottoms liquid fraction pumped in circulation in the tubes of the tube bundle heat transferer.

The fraction of the stripping column liquid which is pumped in circulation is instead superheated in the tubes of the tube bundle heat transferer with respect to the pressure $P_x$ existing above the liquid level of the bottoms liquid in the stripping column, and the boiling process is thus shifted to the passage side of the throttle device (i.e. the contents of the tubes of the tube bundle heat transferer are present in monophasic form; the tube bundle heat transferer functions merely as a superheater). The passage of the "bottoms liquid" thus superheated through the throttle device into the stripping column can be effected directly or indirectly into the stripping column liquid. Under these conditions, the temperature of the liquid stripping column bottoms regularly corresponds to the boiling temperature $T_x$ corresponding to the pressure $P_x$ existing (immediately) above the bottoms liquid. In principle, the passage of the bottoms liquid which has been superheated as described through the throttle device into the stripping column can also be effected above the liquid level of the stripping column bottoms and not directed into it. Under these conditions, the temperature of the liquid stripping column bottoms is regularly below the boiling temperature $T_x$ which accompanies the pressure $P_x$ existing (immediately) above the bottoms liquid. It is essential that the boiling evaporation of the tube bundle heat transferer mounted outside the stripping column does not occur until within the stripping column, i.e. outside the forced-circulation tube bundle heat transferee. The throttling can, as already mentioned, be effected mechanically (diaphragms, valves) and/or hydrostatically (by an appropriately high liquid column above the passage point of the superheated "bottoms liquid"). The temperature in the bottom of the stripping column will typically be from 150 to 180° C., frequently from 160 to 170° C. The temperature on leaving the forced-circulation tube bundle heat transferer is generally at least 5° C. above the bottom withdrawal temperature. The chimney tray in the stripping column is advantageously one which combines the advantageous properties according to DE-A 102 005 009 469 and DE-A 101 598 825. The pump which accomplishes the forced circulation is advantageously one with double-action slip ring seal according to DE-A 102 288 59, the working fluid used, appropriately in accordance with the application, being a glycol/water mixture.

What is essential in the case of the above-described procedure is that the indirect heat exchanger I, with the aid of which the acrylic acid-comprising bottoms liquid withdrawn from the stripping column is heated and hence provides the thermal energy required for the performance of the thermal separating process of "stripping" on the route of the recycling of bottoms liquid heated in this way into the stripping column, can be operated undisturbed for as long as possible, i.e. especially free of fouling of the tube bundle heat transferer tubes. For this purpose, advantageously in accordance with the invention, an active compound recommended in accordance with the invention will be added directly in the bottom of the stripping column. For the above-described specific indirect heat transfer problem, suitable such active compounds are particularly advantageously triethylamine, N,N,N',N'-tetramethyl-1,3-propanediamine and pentamethyldiethylenetriamine. However, all other active compounds recommended in this document are suitable in principle at this point of use. The active compound can be fed into the bottoms liquid of the stripping column in substance or, for example, also dissolved in crude acrylic acid withdrawn via the side draw from the condensation column. Preference is given in accordance with the invention to those solutions which are highly concentrated in the active compound. A typical use amount of inventive active compound in the above-described indirect heat transfer problem is from 0.5 to 1% by weight (but from 0.1 to 10% by weight are also possible), based on the amount of bottoms liquid conducted into the forced-circulation tube bundle flash heat transferee.

Another reason for the advantage of the inventive active compounds is that they are either already ionic compounds or those compounds which are capable of forming ionic compounds with acrylic acid and/or methacrylic acid. Another reason for the advantage of ionic compounds is that they have an elevated boiling point and are therefore capable of accompanying thermal separating processes in particular in a particularly trouble-free manner.

It will be appreciated that the active compounds to be added in accordance with the invention can also be added to the liquid mixtures which comprise at least one (meth)acrylic monomer and are to be heated in accordance with the invention together with the other antifouling agents already recommended in the prior art (especially a surfactant, for example one according to EP-A 1062 197). Useful such surfactants also include those of U.S. Pat. No. 3,271,296 and of GB patent 922 831.

Finally, it should be noted that pure acrylic acid which has been produced by the processes according to documents WO 2004/035514, DE-A 103 327 58, DE-A 102 436 25, WO 2000/53560 and DE-A 102 358 47 and may be off-spec as a result of incorrect operation can be worked up again in a simple manner by feeding it to the above-described stripping column together with high boiler liquid which is to be stripped and has been withdrawn from the condensation column. The acrylic acid additionally supplied to the stripping column in this way is stripped out in the same manner as the acrylic acid present in the high boiler liquid and is recycled as a constituent of the stripping gas which has been withdrawn from the stripping column and is laden with acrylic acid (and, if appropriate) into the bottom of the condensation column (or into the direct cooling of the product gas mixture of the partial oxidation) and hence into the process for recovering pure acrylic acid.

In particular, the present invention comprises the following embodiments according to the invention:

1. A process for transferring heat to a liquid mixture comprising at least one (meth)acrylic monomer with the aid of an indirect heat exchanger which is flowed through on its primary side by a liquid heat carrier and on its secondary side simultaneously by the liquid mixture comprising at least one (meth)acrylic monomer, wherein the liquid mixture comprising at least one (meth)acrylic monomer comprises at least one added active compound other than (meth)acrylic monomers from the group consisting of tertiary amines, the salts formed from a tertiary amine and a Brønsted acid, and quaternary ammonium compounds, with the proviso that none of the tertiary and quaternary nitrogen atoms in the at least one active compound bears a phenyl group but at least some bear at least one alkyl group.

2. A process according to embodiment 1, wherein the at least one (meth)acrylic monomer is acrylic acid and/or methacrylic acid.

3. A process according to embodiment 1, wherein the at least one (meth)acrylic monomer is at least one monomer from the group consisting of hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate and 2-ethylhexyl methacrylate.

4. A process according to any of embodiments 1 to 3, wherein the at least one active compound is a tertiary amine of the general formula

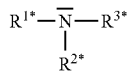

where $R^{1*}$, $R^{2*}$ and $R^{3*}$ are each independently an alkyl group which has from 1 to 8 carbon atoms, or an alkyl group which has from 1 to 8 carbon atoms and in which one or more hydrogen atoms are replaced by at least one of the groups —OH, —NH$_2$, —NHCH$_3$ and —N(CH$_3$)$_2$ and/or the carbon chain is interrupted at least once by an oxygen atom, or a cycloalkyl group which has from 1 to 8 carbon atoms and in which one or more hydrogen atoms are replaced by at least one of the groups —OH, —NH$_2$, —NHCH$_3$ and —N(CH$_3$)$_2$ and/or the cyclic carbon chain is interrupted at least once by an oxygen atom, or is the salt of such a tertiary amine and a Brønsted acid.

5. A process according to any of embodiments 1 to 3, wherein the at least one active compound is a derivative of 1,3-diazole which derives therefrom in that the hydrogen on the nitrogen in the 1-position has been replaced by an alkyl group R$^4$ having from 1 to 8 carbon atoms and/or the nitrogen of the 1,3-diazole in the 3-position has been alkylated with an alkyl group R$^5$ having from 1 to 8 carbon atoms.

6. A process according to any of embodiments 1 to 3, wherein the at least one active compound is the salt of a quaternary ammonium ion, where the quaternary ammonium ion is one of the general formula

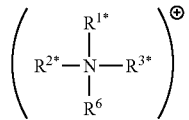

where
R$^{1*}$, R$^{2*}$ and R$^{3*}$ are each independently, and independently of R$^6$, an alkyl group which has from 1 to 8 carbon atoms, or an alkyl group which has from 1 to 8 carbon atoms and in which one or more hydrogen atoms are replaced by at least one of the groups —OH, —NH$_2$, —NHCH$_3$ and —N(CH$_3$)$_2$ and/or the carbon chain is interrupted at least once by an oxygen atom, or a cycloalkyl group which has from 1 to 8 carbon atoms, or a cycloalkyl group which has from 1 to 8 carbon atoms and in which one or more hydrogen atoms are replaced by at least one of the groups —OH, —NH$_2$, —NHCH$_3$ and —N(CH$_3$)$_2$ and/or the cyclic carbon chain is interrupted at least once by an oxygen atom, and
R$^6$, independently of R$^{1*}$, R$^{2*}$ and R$^{3*}$, is an alkyl group having from 1 to 8 carbon atoms.

7. A process according to any of embodiments 1 to 6, wherein the molar mass of the at least one active compound is ≦600 g.

8. A process according to any of embodiments 1 to 7, wherein the liquid mixture comprises an addition of from 0.01 to 10% by weight of its weight of the at least one active compound.

9. A process according to any of embodiments 1 to 8, wherein the liquid mixture comprises ≧0.5% by weight of its weight of the at least one (meth)acrylic monomer.

10. A process according to any of embodiments 1 to 9, wherein the temperature with which the liquid mixture leaves the indirect heat exchanger is from 50 to 350° C.

11. A process according to any of embodiments 1 to 10, wherein the indirect heat exchanger is a tube bundle heat transferee.

12. A process according to any of embodiments 1 to 11, wherein the fluid heat carrier is steam.

13. A process according to any of embodiments 1 to 12, wherein the liquid mixture has been withdrawn from the bottom of a separating column comprising separating internals, into which, in a thermal separating process, at least one stream comprising at least one (meth)acrylic monomer is fed and at least one stream which differs therefrom and comprises at least one (meth)acrylic monomer is withdrawn.

14. A process according to embodiment 13, wherein the liquid mixture, after leaving the indirect heat exchanger, is recycled into the separating column.

15. A process according to embodiment 13 or 14, wherein the at least one stream fed in is the acrylic acid-comprising bottom product of a fractional condensation of the product gas mixture of a heterogeneously catalyzed gas phase partial oxidation of a C$_3$ precursor compound to acrylic acid in a condensation column, and the thermal separating process is the stripping of the acrylic acid from this bottom product.

EXAMPLES AND COMPARATIVE EXAMPLES

Comparative Example 1

An acrylic acid-comprising product gas mixture was withdrawn from a two-stage heterogeneously catalyzed gas-phase partial oxidation of propylene to acrylic acid, and pure acrylic acid was obtained as described in DE-A 10332758 and WO 2004/035514 by subjecting it to a fractional condensation, and the crude acrylic acid withdrawn via a side draw was processed further according to the two aforementioned documents. 2600 kg/h of bottoms liquid were withdrawn from the bottom of the condensation column and had the following contents and a temperature of 109.8° C. (referred to hereinafter as "condensation bottoms liquid"):

| | | |
|---|---|---|
| 42.33 | % by wt. of | acrylic acid, |
| 0.21 | % by wt. of | acetic acid, |
| 0.88 | % by wt. of | water, |
| 97 | ppm by wt. of | formic acid, |
| 9 | ppm by wt. of | formaldehyde, |
| 0.01 | % by wt. of | acrolein, |
| 0.02 | % by wt. of | propionic acid, |
| 0.24 | % by wt. of | furfurals, |
| 12 | ppm by wt. of | allyl acrylate, |
| 1 | ppm by wt. of | allyl formate, |
| 0.26 | ppm by wt. of | benzaldehyde, |
| 6.27 | ppm by wt. of | maleic anhydride, |
| 0.74 | ppm by wt. of | benzoic acid, |
| 0.97 | ppm by wt. of | phthalic anhydride, |
| 20.22 | % by wt. of | diacrylic acid ⎤ Michael adduct, |
| 24.14 | % by wt. of | poly(>2)acrylic acid ⎦ |
| 0.20 | % by wt. of | phenothiazine, |
| 0.66 | % by wt. of | monomethyl ether of hydroquinone (MEHQ), |
| 2.84 | % by wt. of | other high-boiling constituents, and |
| 2 | ppm by wt. of | molecular oxygen. |

A first portion of 1600 kg/h of the aforementioned withdrawn bottoms liquid was fed into the lower portion of a stripping column (material of manufacture=DIN 1.4571 stainless steel) which comprised 50 dual-flow trays (trickle sieve trays) as separating internals. The internal diameter of the stripping column over all dual-flow trays was a uniform 2.4 m. The dual-flow trays were arranged equidistantly in the stripping column, with a separation of 400 mm. Their orifice ratio was a uniform 12%. The hole diameters (some of the hole orifices are covered for adjustment to different column loadings) of the dual-flow trays were a uniform 14 mm (hole arrangement corresponding to strict triangular pitch; distance from hole center to hole center=26 mm (trays 1 to 4 from the bottom), 25.5 mm (trays 5 to 8 from the bottom) and 25 mm (trays 9 to 49 from the bottom) and 25.5 mm (tray 50 from the bottom)). The tray thickness was in each case 4 mm. The lowermost of the dual-flow trays was mounted 7435 mm above the lower end of the column. The stripping column was insulated thermally from the environment. Above the last dual-flow tray, a chimney tray was mounted as a collecting tray. The upper edge of the chimney of this collecting tray was 29 525 mm above the lower column end. The chimneys were roofed and had an internal diameter of 316.7 mm and a height (calculated up to the overflow height without the top) of 1030 mm. Their total number was 12 and they were distributed uniformly over the chimney tray. The collecting tray was configured in single-wall form with a 20 downward gradient and with a lateral side draw and draw stub (DN ~200). The free gas cross section was approx. 30%. 4940 mm above the upper edge of the chimney (calculated without top), six tubes were introduced radially into the column through the column wall, whose internal diameter was 82 mm and whose wall thickness was 2.6 mm. The introduction points of the tubes were distributed equidistantly over the circumference of the column (angle enclosed by two adjacent tubes=600).

At a distance of 500 mm from the inner wall of the column, five of the six tubes were curved downward and ended in a circular nozzle orifice with an internal diameter of 2.5 inches.

The sixth tube had a length of 800 mm reaching from the inner wall of the column radially into the column interior. At a distance of 500 mm from the inner wall of the column, it had a circular nozzle orifice which pointed downward with an internal diameter of likewise 2.5 inches. At the end of the length, this tube had an additional circular nozzle orifice with an internal diameter of 1¼ inches. The central beam of the accompanying spray cone had a vector component directed upward and enclosed an angle of 15° with the vertical to the column cross section. The six tubes were supplied with the liquid for the direct cooling of the gas comprising acrylic acid stripped free, which flowed through the chimney tray, via a ring line which was mounted outside the column and to which the six tubes were attached, and this liquid was sprayed into the column interior. The direct cooling formed condensate which consists predominantly of acrylic acid and was collected on the chimney tray. The length of the stripping column in total (from its lower end up to its upper gas outlet) was 35 260 mm.

The feed of the 1600 kg/h of bottoms liquid withdrawn from the condensation column was at the eighth (8th) dual-flow tray from the bottom.

569 979 kg/h of bottoms liquid, whose temperature was 160° C., were withdrawn from the bottom of the stripping column and had the following contents (referred to hereinafter as "stripping bottoms liquid"):

| | | |
|---|---|---|
| 1.38 | % by wt. of | acrylic acid, |
| 0.02 | % by wt. of | acetic acid, |
| 0.18 | % by wt. of | water, |
| 9 | ppm by wt. of | formic acid, |
| 50 | ppm by wt. of | acrolein, |
| 15 | ppm by wt. of | propionic acid, |
| 0.90 | % by wt. of | furfurals, |
| 0 | ppm by wt. of | allyl acrylate, |
| 1 | ppm by wt. of | allyl formate, |
| 1.13 | ppm by wt. of | benzaldehyde, |
| 27.92 | % by wt. of | maleic anhydride, |
| 3.37 | % by wt. of | benzoic acid, |
| 4.40 | % by wt. of | phthalic anhydride, |

-continued

| | | |
|---|---|---|
| 26.87 | % by wt. of | diacrylic acid |
| 16.99 | % by wt. of | poly(>2)acrylic acid } Michael adduct, |
| 0.92 | % by wt. of | phenothiazine, |
| 2.99 | % by wt. of | MEHQ |
| 12.91 | % by wt. of | other high-boiling constituents, and |
| 1 | ppm by wt. of | molecular oxygen. |

By means of a pump (with double-action slip ring seal according to DE-A 10228859, using a water/glycol mixture as the working fluid), the stripping bottoms liquid withdrawn was pumped into a three-flow tube bundle heat transferee, through whose tubes it flowed (secondary side). The outer tube diameter was 38 mm; the wall thickness of the tubes was 2 mm. The length of the tubes was 4800 mm and the total number of tubes was 234 (in each case 78 tubes for one flow direction). The tube pitch was 48 mm (30° pitch). The cylindrical space surrounding the heat transferer tubes (primary side) was divided into 10 longitudinal sections (segments) by 9 deflecting disks (disk thickness: in each case 5 mm) mounted between the tube plates (in which the exchanger tubes were secured). All 9 deflecting disks were in principle circular. The circle diameter was 859 mm. On each of the circular deflecting disks, however, a half-moon-shaped circle segment had been cut out, whose surface area was 35.8% of the total area, so as to form a corresponding passage for the steam, and these passages were mounted in alternate and opposite succession (otherwise, the deflecting plates were secured with sealing on the vessel wall; where heat transferer tubes met the deflecting plates were corresponding drillholes in the deflecting plates). 1600 kg/h of steam, whose temperature at the inlet was 212° C. and whose inlet pressure was 20 bar, were fed to the space surrounding the heat transferer tubes. The entry of steam and stripping bottoms liquid into the three-flow tube bundle heat transferer were on the same side of the heat transferee.

Only 569 408 kg/h of the heated stripping bottoms liquid which flows out of the three-flow tube bundle heat transferer with a temperature of 165° C. were recycled into the stripping column. The other 570.9 kg/h thereof were degassed, and sent to residue incineration diluted with 79.1 kg/h of methanol. Between the outlet of the heated stripping bottoms liquid from the three-flow tube bundle heat transferer and the reentry point of the heated bottoms liquid into the stripping column, a perforated plate was mounted. This ensured a working pressure of 3 bar upstream of the perforated plate in flow direction, while the working pressure within the stripping columns immediately above the bottoms liquid level was 1.75 bar. The reentry of the heated stripping bottoms liquid was designed as a coaxial double tube drawn into the middle of the stripping column cross section, where it pointed curving downward toward the level of the bottoms liquid and ended just above the surface. The superheated bottoms liquid was conducted in the outer ring of the coaxial double tube; in the center of the coaxial double tube, the stripping gas was simultaneously metered in. This was residual gas withdrawn from the top of the condensation column, which had been compressed (together with cycle gas) to a working pressure of 2.9 bar (with the aid of a multistage radial compressor) and had a temperature of 160° C. Its amount was 28 869.9 kg/h. It had the following contents:

| | | |
|---:|:---|:---|
| 0.28 % by wt. of | acrylic acid, |
| 0.10 % by wt. of | acetic acid, |
| 3.06 % by wt. of | water, |
| 62 ppm by wt. of | formic acid, |
| 0.17 % by wt. of | acrolein, |
| 3 ppm by wt. of | propionic acid, |
| 2 ppm by wt. of | furfurals, |
| 13 ppm by wt. of | allyl formate, |
| 4.72 % by wt. of | molecular oxygen, |
| 2.11 % by wt. of | carbon dioxide, |
| 0.69 % by wt. of | carbon monoxide, |
| 0.65 % by wt. of | propane, |
| 0.32 % by wt. of | propylene, and |
| 87.90 % by wt. of | molecular nitrogen. |

147 877.1 kg/h of condensate were withdrawn from the collecting tray (chimney tray) and had a temperature of 65° C.

The remaining portion of 2600 kg/h of condensation bottoms liquid withdrawn from the condensation column, which amounted to 1000 kg/h, was combined with the aforementioned amount of condensate withdrawn. 13 173.5 kg/h of the resulting liquid mixture, which had a temperature of slightly above 65° C., were recycled into the stripping column as reflux liquid below the chimney tray, but above the uppermost dual-flow tray.

For the purpose of recycling, a distributor tube designed as a continuous circle (mounted centered and horizontally in the column, i.e. parallel to the column cross section) was disposed 770 mm above the uppermost dual-flow tray, and the reflux liquid was fed to it. The internal diameter of the circle was 1870 mm. The external diameter of the tube was 33.7 mm and the internal diameter of the tube was 25 mm.

The distributor tube designed in circular form had 21 hole orifices whose internal diameter was 5 mm. Every second orifice was directed to the underside of the chimney tray in order to keep it moist with reflux liquid. The central jet from the upper half of the orifices pointed at an angle of 45° (relative to the vertical to the column cross section) half downward into the middle of the column and half downward to the column wall.

In addition, on the circumference of the distributor tube in circular form, three precision jet tubes (length=200 mm, external diameter=6 mm, internal diameter=4 mm) were mounted in uniform distribution (enclosing an angle of 120°) and pointing radially outward. The outlet from the precision jet tubes was directed toward ball valves through which washing liquid could be fed to the column. The reflux liquid was fed to the separating portion via the hole orifices and the jet tubes.

It had the following contents:

| | | |
|---:|:---|:---|
| 89.25 % by wt. of | acrylic acid, |
| 0.72 % by wt. of | acetic acid, |
| 5.43 % by wt. of | water, |
| 0.02 % by wt. of | formic acid, |
| 0.04 % by wt. of | acrolein, |
| 0.03 % by wt. of | propionic acid, |
| 0.06 % by wt. of | furfurals, |
| 7 ppm by wt. of | allyl acrylate, |
| 23 ppm by wt. of | allyl formate, |
| 0.03 % by wt. of | benzaldehyde, |
| 0.63 % by wt. of | maleic anhydride, |
| 0.06 % by wt. of | benzoic acid, |
| 0.07 % by wt. of | phthalic anhydride, |

-continued

| | | |
|---:|:---|:---|
| 1.54 % by wt. of | diacrylic acid | ⎫ Michael adducts, |
| 1.83 % by wt. of | polyacrylic acid | ⎭ |
| 0.02 % by wt. of | phenothiazine, |
| 0.05 % by wt. of | MEHQ, |
| 0.21 % by wt. of | other high-boiling constituents, |
| 61 ppm by wt. of | other high-boiling constituents, and |
| 13 ppm by wt. of | molecular oxygen. |

The remaining 135 703.6 kg/h of the liquid mixture having a temperature of 60° C. were conducted through a spiral heat exchanger cooled (in countercurrent) with water (entry temperature=20° C.), which cooled then to 32° C. For the purpose of the direct cooling of the acrylic acid-laden stripping gas ascending in the column through the chimney tray, the total amount of the liquid mixture thus cooled indirectly is sprayed into the stripping column through the double ring distributor described.

At the top of the column, 30 899.0 kg/h of acrylic acid-laden stripping gas were conducted out, which had a pressure of 1.6 bar and a temperature of 60° C. and the following contents:

| | | |
|---:|:---|:---|
| 6.72 % by wt. of | acrylic acid, |
| 0.11 % by wt. of | acetic acid, |
| 2.93 % by wt. of | water, |
| 66 ppm by wt. of | formic acid, |
| 1 ppm by wt. of | formaldehyde, |
| 0.16 % by wt. of | acrolein, |
| 22 ppm by wt. of | propionic acid, |
| 36 ppm by wt. of | furfurals, |
| 1 ppm by wt. of | allyl acrylate, |
| 12 ppm by wt. of | allyl formate, |
| 10 ppm by wt. of | benzaldehyde, |
| 0.01 % by wt. of | maleic anhydride, |
| 4.41 % by wt. of | molecular oxygen, |
| 1.98 % by wt. of | carbon dioxide, |
| 0.65 % by wt. of | carbon monoxide, |
| 0.60 % by wt. of | propane, |
| 0.29 % by wt. of | propylene, and |
| 82.13 % by wt. of | molecular nitrogen. |

It was recycled in its entirety (not immersed) into the bottom region of the condensation column.

After an operating time of 4 days, the above-described operation had to be stopped owing to the extent of fouling which occurred in the tubes of the tube bundle heat transferee, in order to clean the heat transferer tubes to free them of the solid deposits on their inner surface.

Comparative Example 2

The first comparative example was repeated except that the stripping bottoms liquid withdrawn from the stripping column comprised, based on its weight, 1% by weight of added Komad® 313 from Mol (Hungary).

This allowed the operating time to be prolonged to 13 days.

Comparative Example 3

The first comparative example is repeated, except that the stripping bottoms liquid withdrawn from the stripping column comprises, based on its weight, 1% by weight of an added propylene oxide/ethylene oxide block polymer [$(EO)_x(PO)_{56}(EO)_y$, x+y=8] according to EP-A 1 062 197.

This allows the operating time to be prolonged to 14 days.

Example 1

The first comparative example is repeated, except that the stripping bottoms liquid withdrawn from the stripping column comprises, based on its weight, 1% by weight of the added active compound pentamethyldiethylenetriamine:

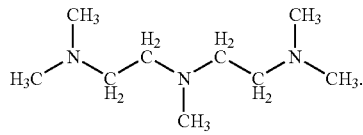

This allows the operating time to be prolonged to 29 days.

Example 2

Like the first example, except that the active compound is N,N,N',N'-tetramethyl-1,3-propanediamine:

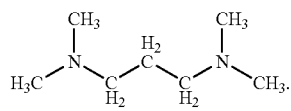

The operating time can be prolonged to 29 days.

Example 3

Like the first example, except that the active compound is triethylamine:

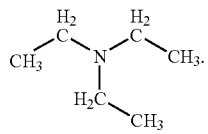

The operating time can be prolonged to 28 days.

Example 4

Like the first example, except that the active compound is N-ethyl-N,N-diisopropylamine:

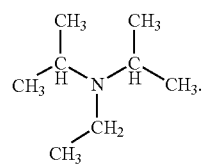

The operating time can be prolonged to 28 days.

Example 5

Like the first example, except that the active compound is N,N,N',N'-tetramethyl-hexanediamine:

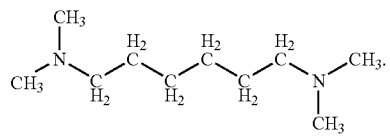

The operating time can be prolonged to 27 days.

Example 6

Like the first example, except that the active compound is bis(2-dimethylaminoethyl)ether:

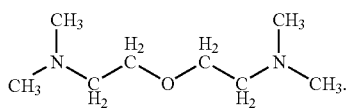

The operating time can be prolonged to 27 days.

Example 7

Like the first example, except that the active compound is 1-methylimidazole:

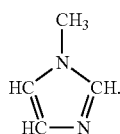

The operating time can be prolonged to 26 days.

Example 8

Like the first example, except that the active compound is N,N-dimethylcyclohexyl-amine. The operating time can be prolonged to 25 days.

Example 9

Like the first example, except that the active compound is tetramethylammonium acetate. The operating time can be prolonged to 29 days.

Example 10

Like the first example, except that the active compound is 1-ethyl-3-methylimidazolium acrylate. The operating time can be prolonged to 29 days.

Example 11

Like the first example, except that the active compound is 1-ethyl-3-methylimidazolium acetate. The operating time can be prolonged to 29 days.

Example 12

Like the first example, except that the active compound is 1-butyl-3-methylimidazolium acetate. The operating time can be prolonged to 28 days.

Example 13

Like the first example, except that the active compound is tetramethylammonium hydroxide. The operating time can be prolonged to 28 days.

Example 14

Like the first example, except that the active compound is tetramethylammonium chloride. The operating time can be prolonged to 27 days.

Example 15

Like the first example, except that the active compound is 1-ethyl-3-methylimidazolium chloride. The operating time can be prolonged to 26 days.

Example 16

Like the first example, except that the stripping bottoms liquid also comprises an added 0.3% by weight of Komad® in addition to the pentamethyldiethylenetriamine. This allows the operating time to be prolonged to 34 days.

The inventive procedure ensures an increased space-time yield of acrylic acid removed.

U.S. Provisional Patent Application No. 60/871,529, filed Dec. 22, 2006, is incorporated into the present patent application by literature reference. With regard to the abovementioned teachings, numerous changes and deviations from the present invention are possible. It can therefore be assumed that the invention, within the scope of the appended claims, can be performed differently from the way described specifically herein.

The invention claimed is:

1. A process for transferring heat to a fluid mixture comprising at least one (meth)acrylic monomer with the aid of an indirect heat exchanger which is flowed through on its primary side by a fluid heat carrier and on its secondary side simultaneously by the fluid mixture comprising at least one (meth)acrylic monomer, wherein the fluid mixture comprising at least one (meth)acrylic monomer comprises at least one added active compound other than (meth)acrylic monomers from the group consisting of tertiary amines, the salts formed from a tertiary amine and a Brønsted acid, and quaternary ammonium compounds, with the proviso that none of the tertiary and quaternary nitrogen atoms in the at least one active compound bears a phenyl group but at least one of the tertiary and quaternary nitrogen atoms in the at least one active compound bears at least one alkyl group.

2. The process according to claim 1, wherein the at least one (meth)acrylic monomer is acrylic acid and/or methacrylic acid.

3. The process according to claim 1, wherein the at least one (meth)acrylic monomer is at least one monomer from the group consisting of hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate and 2-ethylhexyl methacrylate.

4. The process according to any of claims 1 to 3, wherein the at least one active compound is a tertiary amine of the general formula

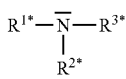

where $R^{1*}$, $R^{2*}$ and $R^{3*}$ are each independently an alkyl group which has from 1 to 8 carbon atoms, or an alkyl group which has from 1 to 8 carbon atoms and in which one or more hydrogen atoms are replaced by at least one of the groups —OH, —$NH_2$, —$NHCH_3$ and —$N(CH_3)_2$ and/or the carbon chain is interrupted at least once by an oxygen atom, or a cycloalkyl group which has from 1 to 8 carbon atoms and in which one or more hydrogen atoms are replaced by at least one of the groups —OH, —$NH_2$, —$NHCH_3$ and —$N(CH_3)_2$ and/or the cyclic carbon chain is interrupted at least once by an oxygen atom, or is the salt of such a tertiary amine and a Brønsted acid.

5. The process according to any of claims 1 to 3, wherein the at least one active compound is a derivative of 1,3-diazole which derives therefrom in that the hydrogen on the nitrogen in the 1-position has been replaced by an alkyl group $R^4$ having from 1 to 8 carbon atoms and/or the nitrogen of the 1,3-diazole in the 3-position has been alkylated with an alkyl group $R^5$ having from 1 to 8 carbon atoms.

6. The process according to any of claims 1 to 3, wherein the at least one active compound is the salt of a quaternary ammonium ion, where the quaternary ammonium ion is one of the general formula

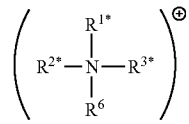

where $R^{1*}$, $R^{2*}$ and $R^{3*}$ are each independently, and independently of $R^6$, an alkyl group which has from 1 to 8 carbon atoms, or an alkyl group which has from 1 to 8 carbon atoms and in which one or more hydrogen atoms are replaced by at least one of the groups —OH, —$NH_2$, —$NHCH_3$ and —$N(CH_3)_2$ and/or the carbon chain is interrupted at least once by an oxygen atom, or a cycloalkyl group which has from 1 to 8 carbon atoms, or a cycloalkyl group which has from 1 to 8 carbon atoms and in which one or more hydrogen atoms are replaced by at least one of the groups —OH, —$NH_2$, —$NHCH_3$ and —$N(CH_3)_2$ and/or the cyclic carbon chain is interrupted at least once by an oxygen atom, and $R^6$, independently of $R^{1*}$, $R^{2*}$ and $R^{3*}$, is an alkyl group having from 1 to 8 carbon atoms.

7. The process according to claim 1, wherein the molar mass of the at least one active compound is ≦600 g.

8. The process according to claim 1, wherein the fluid mixture comprises an addition of from 0.01 to 10% by weight of its weight of the at least one active compound.

9. The process according to claim 1, wherein the fluid mixture comprises ≧0.5% by weight of its weight of the at least one (meth)acrylic monomer.

10. The process according to claim 1, wherein the temperature with which the fluid mixture leaves the indirect heat exchanger is from 50 to 350° C.

11. The process according to claim 1, wherein the indirect heat exchanger is a tube bundle heat transferer.

12. The process according to claim 1, wherein the fluid heat carrier is steam.

13. The process according to claim 1, wherein the fluid mixture has been withdrawn from the bottom of a separating column comprising separating internals, into which, in a thermal separating process, at least one stream comprising at least one (meth)acrylic monomer is fed and at least one stream which differs therefrom and comprises at least one (meth)acrylic monomer is withdrawn.

14. The process according to claim 13, wherein the fluid mixture, after leaving the indirect heat exchanger, is recycled into the separating column.

15. The process according to claim 13 or 14, wherein the at least one stream fed in is the acrylic acid-comprising bottom product of a fractional condensation of the product gas mixture of a heterogeneously catalyzed gas phase partial oxidation of a $C_3$ precursor compound to acrylic acid in a condensation column, and the thermal separating process is the stripping of the acrylic acid from this bottom product.

* * * * *